United States Patent [19]

Pryor et al.

[11] 4,424,144

[45] Jan. 3, 1984

[54] PREPARATION OF BINDERLESS 3A ADSORBENTS

[75] Inventors: James N. Pryor, Catonsville; Chang W. Chi, Columbia, both of Md.

[73] Assignee: W. R. Grace & Co., New York, N.Y.

[21] Appl. No.: 322,003

[22] Filed: Nov. 16, 1981

[51] Int. Cl.³ .............................................. B01J 20/18
[52] U.S. Cl. ..................................... 502/68; 425/112; 425/328; 502/10
[58] Field of Search .................... 252/455 Z; 423/112, 423/328

[56] References Cited

U.S. PATENT DOCUMENTS

| | | | |
|---|---|---|---|
| 3,386,802 | 6/1968 | Michalko | 423/328 |
| 3,679,604 | 7/1972 | Lee et al. | 252/455 Z |
| 3,785,122 | 1/1974 | Yatsurugi et al. | 423/328 X |
| 3,969,276 | 7/1976 | Rosback | 423/112 X |

*Primary Examiner*—Carl F. Dees
*Attorney, Agent, or Firm*—Edward J. Cabic

[57] ABSTRACT

Shaped products of a 3A zeolite are formed either as beads or extrudates without any binder remaining. In the case of beads, a 4A powder is mixed with a caustic solution and a metakaolin clay binder to form beads. The beads are converted to a binderless 4A product which is given a partial calcium exchange followed by a potassium exchange to obtain the desired 3A binderless bead. The 3A extrudates are produced by forming binderless 4A extrudates from a 4A powder and clay mixture that contains 40–60% by weight clay. These binderless 4A extrudates are then given a potassium exchange. Both the beads and the extrudates can be used to dry a mixture of a hydrocarbon compound such as ethylene and water.

12 Claims, No Drawings

PREPARATION OF BINDERLESS 3A ADSORBENTS

CROSS-REFERENCE TO RELATED APPLICATIONS

This invention is an improvement, in part, over the binderless extrudates disclosed in commonly-owned U.S. application Ser. No. 225,075 filed Jan. 14, 1981 now U.S. Pat. No. 4,381,255 and U.S. application Ser. No. 225,076, filed Jan. 14, 1981 now U.S. Pat. No. 4,381,256.

BACKGROUND OF THE INVENTION

1. Field of the Invention

This invention relates to a process to produce binderless 3A adsorbent beads and extrudates from the corresponding product in the 4A form and to the resulting high strength binderless 3A products obtained.

2. Description of the Previously Published Art

Type A zeolites are described in the Milton U.S. Pat. No. 2,882,243. The synthesis procedure using sodium aluminate and sodium silicate results in the sodium form known as the 4A form. Milton teaches converting these 4A powders to the 3A form by exchanging the 4A zeolite with a potassium exchange solution such as a water solution of potassium chloride or dilute potassium hydroxide.

The 3A powder can be mixed with a binder to make formed particles. However, the clay bound particle does not adsorb as much as the same size particle only containing zeolite since the clay binder does not adsorb as much as the zeolite.

Binderless 4A extrudates have been made. In U.S. Pat. No. 3,119,659 Taggart et al discloses reacting a kaolin-type clay with sodium hydroxide to form a preformed body which is then reacted with further sodium hydroxide to yield a completely zeolitic body. Taggart et al also illustrate a method where relatively small amounts of a previously synthesized zeolite are added. The Taggart preferred embodiments only add enough caustic to provide a molar ratio of $Na_2O/SiO_2$ in the range of 0.1 to 0.3. Because they do not initially provide enough caustic in the extrudate for complete conversion of the clay, their method requires a post extrusion treatment in which the extrudates are soaked in caustic liquors in both a digestion step and a heated crystallization step.

This Taggart method requires significant time for the digestion step as well as for a crystallization step, both conducted in their examples in the presence of a sodium hydroxide solution having a concentration of sodium hydroxide significantly greater than the 3% sodium hydroxide solution used in making the precursor 4A extrudates to be used in the present process. Because all of the clay has not reacted before the extrudate is placed in the digestion liquor, there may be some deterioration in structural rigidity of the extrudates when they are placed in the digestion liquid. The Taggart method also requires the extrudates to be dried so the moisture content is less than about 30 weight percent before they can undergo the further sodium hydroxide treatment. Furthermore there is no teaching in Taggart to subsequently exchange these extrudates to obtain a 3A product.

3. Objects of the Invention

It is an object of this invention to produce superior adsorbents in the form of a Type A zeolite which is at least partially potassium exchanged. The adsorbents can be in the form of beads or extrudates and they are characterized by not having any dilution of a binder.

It is a further object to produce a potassium exchanged Type A adsorbent which is particularly suitable for dehydration of olefins.

It is a further object to produce a potassium exchanged Type A adsorbent which has a high water adsorption capacity and rate, excellent resistance to coke formation and good crush strength.

It is a further object to dry hydrocarbon compounds such as ethylene with a binderless 3A adsorbent having a high wet crush strength.

These and further objects will become apparent as the description of the invention proceeds.

SUMMARY OF THE INVENTION

Potassium exchanged binderless 3A zeolite formed particles are obtained with good crush strength by potassium exchanging extrudates and beads made from 4A precursor products.

Beads

In the case of making beads they can be made from a binderless 4A bead. First a synthetic 4A powder is made from sodium silicate and sodium aluminate solutions. The powder is then mixed with a metakaolin binder and a caustic solution to form the beads. Thereafter the metakaolin containing beads are treated with additional sodium hydroxide to convert the metakaolin clay into a 4A zeolite so that the resulting bead is a binderless bead completely made of 4A zeolite. Then according to the present invention this total 4A bead is initially partially exchanged with calcium cations by treating the beads with an aqueous solution containing a calcium salt. This exchange treatment is preferentially only a partial exchange to reduce production costs. The partially calcium exchanged material is then given a potassium exchange with an aqueous solution containing a potassium salt. The resultant product is a bead made of a 3A zeolite and this product has improved crush strength. Note that if the 4A bead had initially been given a potassium exchange without the intermediate calcium exchange, the resulting 3A product would not have the high crush strength exhibited by the 3A bead according to the present invention.

The initial calcium exchange is preferably only partially conducted. After calcium exchange the amount of calcium as measured by CaO can be on the order of 2.0–3 weight percent. If the calcium exchange were carried out more extensively two problems develop. First there will be a waste of calcium since most of the extra amount of calcium added above the 2–3 weight percent level should be re-exchanged out of the zeolite in the potassium exchange and second there will be more potassium required to accomplish the subsequent potassium exchange. In the preferred embodiment the cost of this large amount of wasted calcium is reduced by only partially exchanging with calcium so there will be less calcium wasted during the final potassium exchange step. Extensive calcium exchange of the intermediate product is also not desired because of the difficulty encountered when exchanging calcium with potassium. The more calcium present in the zeolite, the more potassium and thus the higher concentration of potassium required in the exchange solution. The product obtained after potassium exchange contains potassium, sodium and calcium cations, but can still be considered a 3A zeolite in as much as it is capable of excluding ethylene when drying humid ethylene at room temperature. Thus the term 3A zeolite used in this invention includes not only the traditional potassium exchanged form of a sodium containing 4A zeolite, but also the potassium exchanged form that may also have some calcium present, so long as the material is capable of excluding ethylene when drying humid ethylene at room temperature.

Extrudates

In another aspect of the invention it is possible to convert specially produced extrudates directly to the potassium exchanged 3A form without the need to use an initial partial calcium exchange. To do this, the initial binderless 4A extrudate must be made by a special production process as described in copending U.S. application Ser. Nos. 225,075 and 225,076 filed January 14, 1981, the disclosures of which are incorporated herein by reference. The process involves combining approximately 50% by weight of synthetic 4A powder with 50% of a metakaolin binder. To this mixture is added substantial amounts of sodium hydroxide such as on the order of slightly more than the stoichiometric amount of sodium hydroxide required to convert the clay to a 4A zeolite. After extrusion of the mixture the extrudates are allowed to autogeneously react to convert the metakaolin to the 4A zeolite. By employing this specially produced binderless 4A extrudate product, it has now been found possible to directly exchange this material to the 3A form through the use of an aqueous potassium exchange solution. The resultant 3A extrudate also has very good crush strength.

The 3A beads and extrudates can be used as adsorbents in cracked gas drying applications such as the drying of humid ethylene gas. They possess good properties for water adsorption capacity, rate of water adsorption, ethylene exclusion, coking resistance, wet crush strength, and retention of these properties during repeated adsorption cycles.

DETAILED DESCRIPTION OF THE INVENTION

One of the problems this invention has solved is the elimination of the binder diluent in 3A formed particles. If 3A zeolite powder is to be formed into a bead or an extrudate, a binder has been required to hold the powder in shape. Binders are typically clay and they provide no significant adsorption capacity as compared to the 3A zeolite powder. Thus, for any given formed particle there will be some fraction of its weight that is made of a nonfunctioning diluent binder. In addition, the clay binder often acts as a catalyst for coke formation when the clay bound adsorbents are used in cracked gas drying operations.

In the case of 4A formed particles, binderless products have been made. This is possible because the 4A zeolite is a sodium based zeolite. When a metakaolin type clay is used as the binder and sodium hydroxide is added, the caustic upon heating converts the binder to a 4A zeolite. Unfortunately, this clay conversion technique is not possible to use with a 3A potassium exchanged zeolite because when the clay is mixed with the 3A powder the potassium in the zeolite adversely affects the metakaolin conversion.

Binderless 4A beads, made by crystallizing a bead containing a metakaolin type clay binder, a caustic solution, and 4A powder, cannot be successfully converted to a 3A zeolite by subsequently exchanging with an aqueous solution containing a potassium compound. As the beads are subjected to the potassium exchange which reduces the sodium content the wet crush strength of the beads is significantly reduced and the particles are susceptible to breakage during this treatment. This breakage is not acceptable for economic commercial production.

According to the present invention it has been found that a binderless 4A bead may be converted to a binderless 3A bead by first partially exchanging the 4A bead with an aqueous solution containing a calcium compound. Although the 4A bead could be completely exchanged with the calcium, it is preferred to only partially exchange the 4A bead with the calcium solution to reduce production costs. Then this partially calcium exchanged material is given a potassium exchange with an aqueous solution containing a potassium salt. The resultant product is a binderless bead made of a 3A zeolite with improved crush strength compared to clay bound 4A beads.

In the preferred process of the invention the washed 4A beads are first contacted with a calcium chloride solution. The calcium chloride solution is recirculated through the beads in a heated kettle at a temperature of about 160° F. with the liquid recirculating down through beads and back up into the heated container. By recirculating the liquid for about an hour at this temperature a sufficient partial calcium exchange is obtained. In the preferred embodiment the amount of calcium present as measured by CaO is about 2.0–3 weight percent and typically this can be obtained by using a relatively dilute solution such as calcium chloride solution having a calcium content of about 1 weight percent calcium chloride.

These beads are then given a potassium exchange by using the same apparatus with a recirculating potassium salt solution with potassium chloride being the preferred salt. To reduce potassium usage and costs multiple potassium exchange solutions can be used. For example, a first solution having a relatively high concentration such as a 14% potassium chloride solution can be used by recirculating it at about 160° F. for 2 hours. Then the beads can be treated with a second, lower concentration potassium solution such as about a 7% by weight solution of potassium chloride. Again the beads can be given the exchange liquid recirculating treatment at 160° F. for 2 hours with this second solution.

As a result of this series of exchange treatments, the beads retain a high wet strength which results in less than 1% of the product undergoing breakage. Although significant amounts of potassium have been added, there still will be some calcium present in the final product. When measured as CaO it is generally on the order of 2.5 wt. % or less.

The other aspect of the present invention relates to the ability to make 3A extrudates directly from a special form of 4A extrudates. It has been discovered that when 4A binderless extrudates are made from admixture of synthetic 4A zeolite, a metakaolin clay and sodium hydroxide solution where the clay comprises 40–60% by weight of the total weight of the clay and zeolite on a dry basis that the resulting binderless 4A zeolite can be directly exchanged to the 3A form. This exchange is performed by contact with a potassium compound containing solution without having to first go through an intermediate calcium ion exchanged form. This discovery was surprising since in the conversion of beads as described above, it has been found necessary to first go through the calcium exchange intermediate form before the 4A binderless starting product could be converted to the 3A form by using a potassium solution. Thus, when making 4A binderless products from this substantial amount of clay it was completely unexpected that this unique binderless 4A extrudate product could be directly exchanged to the potassium form.

In making the 3A binderless extrudates according to the present invention, one starts with a 4A binderless extrudate that has been made from an extruded mixture of a synthetic 4A zeolite, metakaolin clay present in an amount of 40-60% by weight of the total weight of the zeolite in clay and a sodium hydroxide solution where the amount of sodium hydroxide is in the range of about 90-120% of the stoichiometric amount required to convert the clay to a zeolite. After the mixture has been extruded to form extrudates, these extrudates are aged and treated with a dilute solution of sodium hydroxide at an elevated temperature to complete the crystallization of the aged extrudates. These extrudates are then washed and given the potassium exchange by using an aqueous solution containing a potassium compound such as a potassium salt. A preferred salt is potassium chloride.

The preferred binderless 4A zeolite extrudates which are used as the starting material in the present process to make a 3A product are obtained from a mixture of metakaolin clay and a zeolite such as 4A sieve powder to which has been added a relatively strong caustic solution which contains about the stoichiometric amount or slightly more of caustic required to convert the metakaolin to a 4A zeolite. In these materials there is a substantial amount of clay present which comprises 40-60% of the total mixture. These materials are dry blended together and a complete description of the process is found in U.S. application Ser. Nos. 225,075 and 225,076 identified above. In one embodiment, part of the water used to dilute the caustic solution is added in the form of ice to chill the reaction mixture. After adding a lubricant to aid in extrusion, the mixture is passed through a forming device such as a pellet mill or an extruder having a surrounding jacket which is chilled with cooling water.

The resulting extrudates can be aged from a relatively short period of time, for example about ½ hour, before being lowered into a drum conditioner for length reduction in those instances where a long length extrudate was initially produced. Then the extrudates are aged. In one embodiment, the aging is only required to permit strengthening of the extrudates so that they can withstand the subsequent hydrothermal treatment (wet recrystallization). In another embodiment the extrudates are aged under dry, bulk storage in a container such as a 55 gallon steel drum, a 20 gallon container or a large hopper. As the caustic reacts with the metakaolin clay, the container retains the autogenous heat which develops in the central part of the bulk to gradually increase the temperature sufficient to initiate the crystallization process at which point there will result a substantial conversion of the remaining clay to the crystalline zeolite form.

After the aging has taken place by either of the two embodiments, the extrudates are treated with a heated solution of very dilute sodium hydroxide solution, such as, for example, about a 3% sodium hydroxide, to further insure complete crystallization.

The crystallized extrudates can then be washed to remove excess unreacted sodium and then treated before drying with a potassium containing solution to produce a zeolite with a pore diameter of nominal 3 Angstrom units according to the present invention. After the potassium exchange treatment, the treated extrudates are dried and then calcined to activate the sieves.

The blend ratio of clay to zeolite and the amount of caustic usage can be optimized to prevent impurity formation while generating an intermediate 4A extrudate of high strength for the subsequent wet crystallization step in a dilute caustic solution. This results in a final superior sieve product.

In a preferred embodiment the poatassium exchange takes place in two steps. In the first step a relatively concentrated solution such as a 14% potassium chloride solution is used in an amount of about 4.5 lbs. of solution per lb. of dry extrudate to treat the extrudates in a heated container with the solution being recirculated through the container and the system maintained at a temperature of about 160° F. This first recirculation treatment can be done for approximately 1 hour.

After these extrudates have been given this initial treatment to remove the sodium, they are then treated with a second solution having a lower concentration of potassium chloride. Again a preferred solution is one containing only about 7% by weight of potassium chloride in an amount of about 4.3 lbs. of solution per lb. of dry extrudate. This solution is also used in the same heated reactor with the liquid passing down through the reactor and the recirculated back into the top of the reactor. After treatment with this second solution at a temperature of 160° F. for 2 hours, the product is adequately exchanged to the 3A form. Next the product is washed, dried at 210° F. and calcined at 1050° F. for 2 hours. During this exchange operation less than 1% of the product underwent breakage which illustrates the strong wet crush strength that these material possess.

The 3A products obtained are evaluated by various tests. The water capacity is a key feature since the greater the amount of water adsorbed, the better the adsorbent. This property is a function of the amount of zeolite present. By avoiding the presence of any binder the present product can adsorb more water.

Water adsorption rate is also important to the efficiency of an adsorbent in a fixed bed adsorber. Mass transfer zone length (MTZ) is a useful measure of the adsorption rate that directly relates to the efficiency of the adsorbent in a fixed bed operation. The shorter the MTZ the more rapid and efficient the adsorption process. See generally, "Mass Transfer Operations" by R. E. Treybal (McGraw-Hill 2nd ed. 1968) for a discussion of adsorption zone heights.

Ethylene exclusion is an important property. If ethylene and other olefins are adsorbed onto the internal surfaces of the 3A zeolite, then they can polymerize and coke to some extent under thermal cycling such as occurs within an ethylene drier. If this happens, both the $H_2O$ capacity and mass transfer properties of the adsorbent will be detrimentally affected. In addition, simple adsorption of organic species on the 3A adsorbent during the drying process means that these organic molecules will have to be displaced by water molecules later in order for the $H_2O$ to be adsorbed. This displacement adsorption and associated counter diffusion significantly reduces the overall $H_2O$ adsorption rate compared to the situation where ethylene is totally excluded by the 3A zeolite.

Since ethylene adsorption is generally very low, additional zeolite pore size information is gained by measuring the asorption of a slightly smaller diameter molecule, $CO_2$. These measurements were made at 250 torr and 25° C.

Coking resistance is a desired property of the adsorbent. By preventing the ethylene from entering the 3A zeolite the coking can be prevented. When adsorbents containing clay binders are used, the coking rate will be dependent on the binder type and amount. The present binderless products do not have any clay binder and thus have improved coking resistance.

The wet crush strength is a method to predict the ability of the adsorbent to withstand the hydrothermal shock that wet particles undergo in the regeneration process. This shock produces internal stress which is the primary cause of adsorbent breakage. Particle breakage is to be avoided since it increases the pressure drop across the adsorbent column and it can cause non-uniform gas flow through the adsorbent bed which results in premature $H_2O$ breakthrough so as to lower the dynamic capacity. The present binderless 3A products have improved wet crush strength compared to 3A products with binders present.

TEST PROCEDURES

In evaluating the 3A adsorbents the following tests were used.

Wet Crush Strength

Adsorbent wet crush strengths were determined after a ten minute exposure to liquid $H_2O$.

Water Adsorption Capacity

Equilibrium $H_2O$ capacities at 10, 20, 40, 60 and 80% relative humidity, R.H., were determined. The water capacities are given as the sum of measured $H_2O$ adsorption capacity and the total volatility as measured at 1750° F. to ensure a valid comparison.

Water Adsorption Rate

Dynamic capacities and MTZ length were determined with a high pressure adsorbent evaluation unit using saturated natural gas. High superficial velocities were used to shorten the duration of the test and magnify differences in mass transfer rate.

Ethylene Exclusion

Ethylene adsorption was determined using a Cahn balance. Measurements were made after a one hour exposure to $C_2H_4$ at 760 torr and 25° C.

Coking Resistance

The following accelerated coking test was used. A 20 gram sample is heated to 600° F. in a sealed bomb under a flow of $N_2$ to purge the system. After 2 hours at 600° F., the $N_2$ flow is stopped and the $N_2$ removed from the bomb using a roughing vacuum line. While maintaining the bomb at 600° F., butadiene is introduced to a pressure of 760 torr (absolute). After one hour the bomb is again evacuated and repressurized with butadiene. This cycle is repeated 16 times after which the bomb is again purged with $N_2$. The sample is then given a carbon analysis.

Dynamic Capacity for Drying Moist Ethylene

The dynamic capacity is a measure of the useful capacity of the adsorbent in its normal cyclic operation. It is calculated by determining the total mass of water removed from the moist ethylene feed at the time at which the outlet humidity reached is 10% of the inlet humidity and dividing this amount of removed water by the initial mass of the adsorbent and expressing the quotient as a percent by multiplying by 100. The higher the value the better adsorbent performance.

Saturation Capacity for Drying Moist Ethylene

The saturation capacity relates to the total amount of water adsorbed if the adsorbent bed is allowed to equilibrate with the moist feed. It is calculated by determining the total mass of water removed from the moist ethylene feed at the time at which the outlet humidity finally reaches the inlet humidity. The value is obtained by dividing this amount of removed water by the mass of the initial adsorbent and expressing the quotient as a percent by multiplying by 100.

The binderless 3A product obtained according to the present invention in either the bead or the extrudate form can be used to dry hydrocarbon compounds when mixed with water. Preferred compounds include the olefins and especially ethylene gas. The binderless zeolite is able to adsorb the water while hardly adsorbing any hydrocarbon compound such as ethylene gas. These adsorbent materials have high adsorption capacities and excellent mass transfer properties.

Having described the basic aspects of our invention, the following examples are given to illustrate specific embodiments thereof.

EXAMPLE 1

This example illustrates the generalized procedure for the production of the binderless 4A beads to be used as the starting material in the present process.

Wet, crystallized 4A beads are prepared by mixing 4A powder and metakaolin in weight ratio of 4:1 and then beading the material in a pelletizing mixer while dampening the mix with an 18% NaOH in $H_2O$ solution. At the end of the beading process the roughly 4 to 8 mesh beads contain 0.13 lbs NaOH per lb NaA and 0.91 lbs $H_2O$ per lb NaA.

These beads are allowed to stand overnight during which time they develop increased crush strength. The beads are then placed in a 3% NaOH $H_2O$ solution; 1.6 pounds solution per lb of beads (including $H_2O$ in beads). The solution is heated and maintained at 250° F. and recirculated through the beads for 4 hours. During this process the metakaolin portion of the beads crystallize to NaA zeolite. The beads are then drained and washed with water at 120° F.

EXAMPLE 2

This example illustrates the exchange procedure according to the present invention to convert 4A beads to 3A beads.

Three exchange solutions were prepared. Solution I was made by dissolving 0.0688 lbs. of calcium chloride, $CaCl_2$, in 6.60 lbs. of water.

Solution II was prepared by dissolving 0.936 lb. of potassium chloride, KCl, into 6.60 lbs. of water.

Solution III was prepared by dissolving 0.467 lb. of KCl in 6.60 lbs. of water.

In the first step of the procedure the beads were treated with the calcium chloride Solution I. Approximately 2.43 lbs. of washed, crystallized 4A beads made in a manner similar to the process of Example 1 were added to Solution I described above. This amount of 4A beads correspond to approximately to 1.65 pounds on a dry basis.

The mixture of beads and solution was heated in a heated kettle to 160° F. Through a tubular screen extending up from the bottom drain the solution was recirculated by passing through the screen, down the drain and through a pump back into the kettle. The screen kept the beads in the kettle and the recirculation was maintained for 1 hour.

Thereafter, Solution I was drained from the beads and Solution II was added to the kettle. Again this solution and bead mixture were heated to 160° F. and the solution was recirculated for 2 hours.

In the next step Solution II was drained from the beads and Solution III was added. This solution and the beads were again heated to 160° F. and the solution was recirculated for 2 hours.

After draining off Solution III the beads were washed and dried at 210° F. Finally, the dry beads were calcined for 2 hours at a temperature of 1050° F.

During the exchange procedures, less than 1% of the product underwent breakage. The final product had a calcium content as measured by CaO of 2.5 wt. %.

The evaluation of the product for chemical composition, physical and adsorptive properties as well as selectivity in coking tendency are set forth in Table I.

Comparable test data is also set forth in Table I for a typical clay bound 3A product.

TABLE I

Comparative Evaluation of 3A Adsorbents

| | Binderless 3A Beads | Binderless 3A Extr. | Control Typical Clay Bound 3A Beads |
|---|---|---|---|
| Physical | | | |
| Binder | None | None | Yes |
| Size/Shape | 4–8 mesh beads | 1/16" diam. Extr. | 4–8 mesh beads |
| Density, lbs./ft$^3$ | 43.0 | 42.5 | 44.6 |
| Crush Strength, lbs., | | | |
| Dry | 15.0 | 7.9 | 13.6 |
| Wet | 3.7 | 4.5 | 2.7 |
| Absorptive | | | |
| H$_2$O, wt. % | | | |
| 10% RH | 22.7 | 22.4 | 20.4 |
| 20% | 23.5 | 23.3 | 21.3 |
| 40% | 24.3 | 24.3 | 22.0 |
| 60% | 25.0 | 24.8 | 22.6 |
| 80% | 25.7 | 25.6 | 23.8 |
| H$_2$O Dynamic | | | |
| Saturation Capacity, wt. % | 23.1 | 23.0 | 21.4 |
| MTZ Length, ft. | 2.95 | 2.80 | 3.65 |
| C$_2$H$_4$, 760 torr, 25° C., wt. % | .01 | .00 | .03 |
| Catalytic | | | |
| % Carbon After Butadiene Cycling | 1.05 | .95 | 2.06 |

From a comparison of these two materials it is seen the superiority of the present product because of the higher wet and dry crush strength, higher adsorption capacity, faster adsorption rate as measure by the MTZ, better ethylene exclusion and greater resistance to coking.

EXAMPLE 3

This is a comparison example to illustrate the poor crush strength obtained when 4A beads are directly exchanged with a potassium solution.

The 4A binderless beads made by a procedure similar to Example 1 had a Na$_2$O content of 21.8% and a wet crush strength of 7.4 lb. The beads were treated with a potassium chloride solution to replace the sodium. After the Na$_2$O content had been reduced to about 11% the wet crush strength was reduced to 1.7 lb. Breakage of adsorbent particles is observed at this point in the potassium exchange process. As a result this procedure is not suitable for a high yield commercial process.

EXAMPLE 4

This example illustrates the production of wet crystallized binderless 4A extrusions to be used as the starting material for the direct conversion to a 3A binderless extrudate.

A 50—50 mixture of synthetic 4A powder and metakaolin on a dry basis was used to make 1/16" extrudates. On a basis of 100 pounds of dry blend, 50 pounds of Hi-Opaque clay, a metakaolin clay obtained from Freeport Kaolin, was measured out along with 62.5 pounds of 4A zeolite powder since the powder had a 20% moisture content. These two ingredients were charged to a sigma mixer, 1 pound of Sterotex powder was added and the resulting mixture was blended together.

In another tank a caustic solution was prepared by diluting 40 pounds of a commercially available 50% caustic solution with 25.5 pounds of water and 36.5 pounds of ice to cool the mixture.

To facilitate the mixing of the dry powder and liquid, a paste was made from about 70% of the blended powder added to all of the chilled caustic solution. The past was mixed intensively for about 10 minutes and then the remaining 30% of the blended powder was added and admixed for an additional 15 minutes.

Minor adjustment of the moisture content can be made at this point either by adding more blended powder or water. The heel should have an Ohaus of 35–36% at 800° F. In this example the actual value obtained was 36.0%.

This material was then fed into an auger type extruder having a barrel surrounding the extruder through which chilled water was passed. This was done by forming a mixture of ice, water and rock salt and the resulting water solution at a temperature below 32° F. was continuously recirculated around the barrel with a small pump.

The extrudates were aged in a thin bed on a try for at least 2 days to give them sufficient strength to withstand the subsequent crystallization treatment in a boiling 3% NaOH solution where they were treated for about 4 hours. They were washed.

Another portion was washed, dried and calcined at a temperature of 1000° F. for a period of 2 hours. A crystalline analysis made by X-ray diffraction showed nearly complete conversion to zeolite A with no other phases present.

EXAMPLE 5

This example illustrates the direct potassium exchange with the 4A extrusions made in Example 4 to obtain 3A extrudates.

Two solutions were prepared. The first Solution I contained 5.67 lbs. of KCl, dissolved in 40 lbs. of water.

Solution II was made by dissolving 2.83 lbs. of KCl in 40 lbs. of water.

The procedure involved adding 14.7 lbs. of washed, crystallized 4A extrusions made by the process of Example 4 which corresponded to 10.0 lbs. on a dry basis to Solution I. The mixture of extrusions and solution was heated to 160° F. and this solution was recirculated for 1 hour in the heated kettle apparatus described in Example 2.

Next Solution I was drained and all of the more dilute potassium chloride Solution II described above was added. Again the mixture of the extrudates and Solution II was heated to 160° F. and this solution was recirculated for 2 hours. Thereafter, Solution II was drained and the resulting product was washed and dried at 210° F. The dried product was then calcined for 2 hours at 1050° F. Again, during the exchanging process less than 1% of the product underwent breakage. The product was evaluated and the results are set forth in Table I. Again superior results are obtained which are better than the clay bound beads.

EXAMPLE 6

This example illustrates the drying of moist ethylene gas using 3A extrudates according to this invention.

3A extrudates were made according to the procedure of Examples 4 and 5 with the exception that in run A the extrudates had a diameter of slightly larger than $\frac{1}{8}$" and in run B the diameter was 3/32". As a control the 4–8 mesh clay bound beads described in Example 2 were also used.

The pilot scale evaluation of these adsorbents for ethylene dehydration involved placing the active adsorbent in an 8 foot column having an inside diameter of 1 inch and passing ethylene gas at a pressure of 350 psig, a temperature of 72° F. and a relative humidity of 97% through the column at a superficial velocity of 57 ft./min. The outlet humidity was measured as a function of time. The dynamic adsorption properties of these materials are set forth in Table 2 below.

The dynamic capacity and saturation capacity test procedures have been described earlier. The higher the value of the dynamic capacity the better the adsorbent performance. The MTZ, the mass transfer zone length, has also been defined earlier. Again the shorter the length, the better the adsorbent performance.

TABLE 2

|  | Run A | Run B | Control |
| --- | --- | --- | --- |
| material size/shape | $\frac{1}{8}$" extrudate | 3/32" extrudate | 4–8 mesh bead |
| Dynamic Capacity (wt. %) | 19.4 | 21.2 | 17.6 |
| Saturation Capacity (wt. %) | 24.2 | 23.8 | 21.7 |
| MTZ (ft.) | 2.9 | 1.5 | 3.0 |

It is understood that the foregoing detailed description is given merely by way of illustration and that many variations may be made therein without departing from the spirit of this invention.

We claim:

1. A process of making 3A zeolite binderless beads comprising
    forming beads from a mixture of 4A zeolite powder, a clay binder and a sodium hydroxide solution;
    treating the beads with additional sodium hydroxide to convert the clay binder to a 4A zeolite to provide a 4A binderless bead;
    partially exchanging the 4A binderless bead with a calcium containing solution to form an intermediate bead product;
    exchanging the intermediate bead product with a potassium exchanging solution selected from the group consisting of an aqueous solution of a potassium salt, a potassium hydroxide solution and mixtures thereof to obtain a 3A zeolite binderless bead; and
    recovering and activating the potassium exchanged bead product.
2. The process according to claim 1, wherein the recovering and activating step comprises washing the potassium exchanged beads, drying and calcining to remove adsorbed water.
3. The process according to claim 1, wherein the potassium exchange solution is an aqueous solution of potassium chloride.
4. The process according to claim 1, wherein the partial calcium exchange is carried out so that the intermediate bead product has a calcium content, measured as CaO, of about 2.0 –3.0 wt. %.
5. The process according to claim 1, wherein the clay is a metakaolin clay.
6. The adsorbent 3A binderless bead made by the process of claim 1.
7. A process for making a binderless 3A extrudate from an extrudable mixture of a synthetic 4A zeolite, metakaolin clay, and sodium hydroxide solution, said clay comprising about 40–60% by weight of the total weight of the clay and the zeolite on a dry basis and the amount of sodium hydroxide being in the range of about 90–120% of the stoichiometric amount to convert the clay to a zeolite, said process comprising
    extruding the extrudable mixture to form extrudates;
    aging the extrudates;
    treating the aged extrudates with a dilute solution of sodium hydroxide at an elevated temperature to complete the crystallization of the aged extrudates;
    washing the crystallized extrudates;
    contacting the washed extrudates with a potassium exchanging solution selected from the group consisting of an aqueous solution of a potassium salt, a potassium hydroxide solution and mixtures thereof; and
    recovering and activating the potassium exchanged extrudate product.
8. The process according to claim 7, wherein the recovering and activating step comprises washing the potassium exchanged beads, drying and calcining to remove adsorbed water.
9. The process according to claim 7, wherein the potassium exchange solution is an aqueous solution of potassium chloride.
10. The adsorbent 3A binderless extrudate made by the process of claim 7.
11. A 3A binderless bead adsorbent made from a mixture of metakaolin clay and a synthetic 4A zeolite where the clay is present from about 40–60% by weight on a dry basis of the total weight of the clay and zeolite.
12. A 3A binderless extrudate adsorbent made from a mixture of metakaolin clay and a synthetic 4A zeolite where the clay is present from about 40–60% by weight on a dry basis of the total weight of the clay and zeolite.

* * * * *